United States Patent [19]

Goldberg et al.

[11] Patent Number: 4,980,160
[45] Date of Patent: Dec. 25, 1990

[54] COMBINATIONS OF TUMOR NECROSIS FACTORS AND ANTI-INFLAMMATORY AGENTS AND METHODS FOR TREATING MALIGNANT AND NON-MALIGNANT DISEASES

[75] Inventors: Alfred L. Goldberg, Brookline, Mass.; Walter C. Fiers, Destelbergen, Belgium; Isis C. Kettelhut, Brookline, Mass.

[73] Assignees: Biogen, Inc.; President and Fellows of Harvard College, both of Cambridge, Mass.

[21] Appl. No.: 373,646

[22] Filed: Jun. 29, 1989

Related U.S. Application Data

[63] Continuation of Ser. No. 919,851, Oct. 16, 1986, abandoned.

[51] Int. Cl.$^5$ .............................................. A61K 37/00
[52] U.S. Cl. ........................................ 424/85.1; 514/2; 514/8; 514/21; 514/886; 530/351
[58] Field of Search .................... 514/2, 8, 21, 886; 424/85.1; 530/351

[56] References Cited

U.S. PATENT DOCUMENTS

| | | | |
|---|---|---|---|
| 4,500,540 | 2/1985 | Hamilton et al. | 514/399 |
| 4,650,674 | 3/1987 | Aggarwal et al. | 424/85.1 |
| 4,791,101 | 12/1988 | Adolf | 424/85.1 |
| 4,822,605 | 4/1989 | Powell | 424/85.2 |
| 4,857,314 | 8/1989 | O'Connor et al. | 530/351 |
| 4,863,727 | 9/1989 | Zimmerman | 530/351 |
| 4,879,111 | 11/1989 | Chang | 424/852 |
| 4,894,225 | 1/1989 | Zimmerman | 424/85.1 |

OTHER PUBLICATIONS

Ghiara, *Immunol* 139, 1987, pp. 3676–3679.
Alexander et al., *CA vol.* 107, 1987, #327449.
Watanabe et al., *CA* vol. 108, 1988 #87353n.
Conti et al., *Int. J. Immunopharmae* vol. 10 1988, pp. 907–911.
Kull et al., *Concer Res.* vol. 41, 1981, pp. 4885–4890.
Baldwell et al., *Cancer Res.* vol. 46, 1986, pp. 3990–3993.
Beutler et al., *Science* 229, 1985, pp. 869–871.
Beutler et al. *Nature* 320, 1986, pp. 584–588.
Kawakawi et al., *Biochem. Brophys. Res. Comm.* 141 (2) 1986, pp. 482–487.
Bachwich et al., *Biochem. Biophys. Res. Comm.*, 136(1) 1986, pp. 94–101.
Kunhel et al., *Biochem. Biophys. Res. Comm*, 137(1) 1986, pp. 404–410.
P. M. Almqvist et al. "Treatment of Experimental Canine Endotoxin Shock with Ibuprofen, a Cyclooygenase Inhibitor," *Circulatory Shock*, 13, pp. 227–232 (1984).
F. R. Balkwill et al., "Human Tumor Xenografts Treated with Recombinant Human Tumor Necrosis Factor Alone or in Combination with Interferons," *Cancer Research*, 46, pp. 3990–3993 (1986).
H. Bult et al., "Blood Levels of 6-Keto-PGF$_{1\alpha}$, the Stable Metabolite of Prostacyclin during Endotoxin-Induced Hypotension," *Arch. Int. Pharmacodyn.*, 236, pp. 285–286 (1978).

(List continued on next page.)

*Primary Examiner*—Garnette D. Draper
*Attorney, Agent, or Firm*—James F. Haley, Jr.; Leon R. Yankwich; Jane A. Massaro

[57] ABSTRACT

This invention relates to combinations and methods for the treatment of malignant and non-malignant diseases. More particularly, this invention relates to combinations of natural or recombinant tumor necrosis factors ("TNF") and non-steroidal anti-inflammatory agents, such as indomethacin and ibuprofen, useful for the growth inhibition or killing of transformed cells. According to this invention, the non-steroidal anti-inflammatory agents are used to reduce or eliminate the toxic side effects of high doses of TNFs employed in the treatment of malignant and non-malignant neoplastic diseases. Advantageously, the combinations and methods of this invention allow the administration of higher doses of TNF than those tolerated in conventional treatment regimens based upon TNF alone.

18 Claims, 4 Drawing Sheets

OTHER PUBLICATIONS

E. A. Carswell et al., "An Endotoxin-Induced Serum Factor that causes Necrosis of Tumors," *Proc. Nat. Acad. Sci. U.S.A.*, 72, pp. 3666-3670 (1975).

J. A. Cook et al., "Elevated Thromboxane Levels in the Rat during Endotoxic Shock; Protective Effects of Imidazole, 13-Azaprostanoic Acid, or Essential Fatty Acid Deficiency," *J. Clin. Invest.*, 65, pp. 227-230 (1980).

J. M. Dayer et al., "Cachetin/Tumor Necrosis Factor Stimulates Collagenase and Prostaglandin $E_2$ Production by Human Synovial Cells and Dermal Fibroblasts," *J. Exp. Med.*, 162, pp. 2163-2168 (1985).

J. R. Fletcher in *Biological Protection with Prostaglandins*, I, pp. 65-72 (1985).

P. V. Halushka et al., "Protective Effects of Aspirin in Endotoxic Shock," *J. Pharm. and Exper. Thera.*, 218, pp. 464-469 (1981).

K. Haranaka et al., "Antitumor Activity of Murine Tumor Necrosis Factor (TNF) against Transplanted Murine Tumors and Heterotransplanted Human Tumors in Nude Mice," *Int. J. Cancer*, 34, pp. 263-267 (1984).

T. Kudo et al., "Antitumor Activity of Indomethacin on on Methylazoxymethanol-induced Large Bowel Tumors in Rats," *Gann*, 71, pp. 260-264 (1980).

L. J. Old, "Tumor Necrosis Factor (TNF)," *Science*, 230, pp. 630-632 (1985).

N. O. Olsson et al., "Effect of Indomethacin on the Growth of Colon Cancer Cells in Syngeneic Rats," *Int. J. Immunopharmac.*, 6, pp. 329-334 (1984).

J. R. Parratt and R. M. Sturgess, "E. Coli Endotoxin Shock in the Cat; Treatment with Indomethacin," *Br. J. Pharmac.*, 53, pp. 485-488 (1975).

M. Pollard and P. H. Luckert, "Prolonged Antitumor Effect of Indomethacin on Autochthonous Intestinal Tumors in Rats," *JNCI*, 70, pp. 1103-1105 (1983).

T. Shirai et al., "Cloning and Expression in *Escherichia coli* of the Gene for Human Tumor Necrosis Factor," *Nature*, 313, pp. 803-806 (1985).

B. L. Short et al., "Indomethacin Improves Survival in Gram-Negative Sepsis," *Advances in Shock Research*, 6, pp. 27-36 (1981).

"Tumor Necrosis Factor Less Toxic in Trials," *Medical World News* (Oct. 13, 1986).

J. Wan and R. F. Grimble, "Inhibitory Effects of Indomethacin on some features of the Metabolic response to *Escherichia coli* Endotoxin in Rats," *Proc. Nutritional Soc.*, 45, p. 51A (1986).

A. M. Wang et al., "Molecular Cloning of the Complementary DNA for Human Tumor Necrosis Factor," *Science*, 228, pp. 149-154 (1985).

B. D. Williamson et al., "Human Tumor Necrosis Factor produced by Human B-Cell Lines: Synergistic Cytotoxic Interaction with Human Interferon," *Proc. Natl. Acad. Sci. U.S.A.*, 80, pp. 5397-5401 (1983).

W. C. Wise et al., "Implications for Thromboxane $A_2$ in the Pathogenesis of Endotoxic Shock," *Advances in Shock Research*, 6, pp. 83-91 (1981).

COMBINATIONS OF TUMOR NECROSIS FACTORS AND ANTI-INFLAMMATORY AGENTS AND METHODS FOR TREATING MALIGNANT AND NON-MALIGNANT DISEASES

This is a continuation of application Ser. No. 919,851, filed Oct. 16, 1986, entitled, COMBINATIONS OF TUMOR NECROSIS FACTORS AND ANTI-INFLAMMATORY AGENTS AND METHODS FOR TREATING MALIGNANT AND NON-MALIGNANT DISEASES, now abandoned.

TECHNICAL FIELD OF INVENTION

This invention relates to combinations and methods for the treatment of malignant and non-malignant diseases. More particularly, this invention relates to combinations of natural or recombinant tumor necrosis factors ("TNF") and non-steroidal anti-inflammatory agents, such as indomethacin and ibuprofen, useful for the growth inhibition or killing of transformed cells. According to this invention, the non-steroidal anti-inflammatory agents are used to reduce or eliminate the toxic side effects of high doses of TNFs employed in the treatment of malignant and non-malignant neoplastic diseases. Advantageously, the combinations and methods of this invention allow the administration of higher doses of TNF than those tolerated in conventional treatment regimens based upon TNF alone.

BACKGROUND ART

TNF is a protein produced by macrophages and mononuclear phagocytes upon activation by endotoxin or other microbial products or stimuli [E. A. Carswell et al., "An Endotoxin-Induced Serum Factor That Causes Necrosis Of Tumors", *Proc. Natl. Acad. Sci. USA*, 72, pp. 3666–70 (1975); P. J. Hotez et al., "Lipoprotein Lipase Suppression In 3T3-L1 Cells By A Haematoprotozoan-Induced Mediator From Peritoneal Exudate Cells", *Parasite Immunol.*, 6, pp. 203–09 (1984)]. Although TNF is cytotoxic or cytostatic for a broad range of animal and human cancer cells in vitro and induces hemorrhagic necrosis in certain animal tumors and heterotransplanted human tumors in vivo, it exerts little or no cytotoxicity on normal cells [K. Haranaka and N. Satomi, "Note: Cytotoxic Activity Of Tumor Necrosis Factor (TNF) On Human Cancer Cells In Vitro", *Japan J. Exp. Med.*, 51, pp. 191–94 (1981); L. Old, "Cancer Immunology: The Search For Specificity - G.H.A. Clowes Memorial Lecture", *Cancer Research*, 41, pp. 361–75 (1981); B. D. Williamson et al., *Proc. Natl. Acad. Sci. USA*, 80, pp. 5397–401 (1983)].

Malignant diseases are a group of diseases characterized by tumorigenic or neoplastic cell growth. Such diseases include malignant hematological systemic diseases, carcinomas, sarcomas, myelomas, melanomas, lymphomas and papillomas. Non-malignant neoplastic diseases, including non-malignant tumors, are also characterized by neoplastic cell growth which is localized to a specific area. The transformation of normal cells within the body into either malignant or non-malignant neoplasms may be induced by chemical carcinogens, radiation, physical agents or spontaneous tumorigenic growth.

The precise etiology of many malignant and non-malignant diseases remains unknown. Accordingly, treatments for these diseases are limited, and effective agents are not always conventionally available for a specific disease. Such diseases have been treated, for example, by surgical techniques or by non-surgical methods including chemotherapy, radiation and immunotherapy. Any value of such treatment techniques, however, is often diminished by adverse side effects or risks attendant with their use. For example, non-surgical techniques such as chemotherapy generally have immunosuppressant effects and may increase the patient's susceptibility to secondary infections. Surgical treatments to excise malignant or non-malignant tumors involve risks which accompany any invasive procedure and may not effectively remove or eliminate the entire transformed cell population. Moreover, certain malignant diseases are resistant to conventional treatment techniques. For example, most skin melanomas are considered to be radio-resistant. No single agent or combination chemotherapy has been successful in effecting consistent regressions of malignant melanomas. Malignant renal cell carcinoma is also resistant to available single agent and combination chemotherapies.

Alternative methods of treatment for malignant and non-malignant diseases have involved the use of monoclonal antibodies to tumor-specific antigens on the surface of transformed cells. The effectiveness of such treatments, typically involving murine monoclonal antibodies, is often limited by a variety of factors, including anti-antibody responses which impede the effectiveness of further administrations of the murine antibody [G. E. Goodman et al., "Pilot Trial Of Murine Monoclonal Antibodies In Patients With Advanced Melanoma", *J. Clin. Oncol.*, 3, pp. 340–51 (1985)]. Other reported side effects of monoclonal antibody treatments include anaphylaxis, fever and chills.

In view of the disadvantages of such therapies, various treatments have been directed to augmenting the body's immune response to tumorigenic cells by increasing the body's level of certain lymphokines. For example, TNF alone is known to inhibit the growth of or to kill tumor cells. In addition, combinations of human lymphotoxin and human gamma interferon have been reported to inhibit tumor growth [European patent application 128,009]. Combinations of TNF and human interferon have also been reported to demonstrate a greater growth inhibitory or cytotoxic effect on human tumors than the sum of their separate effects [L. Fransen et al., "Recombinant Tumor Necrosis Factor: Its Effect And Its Synergism With Interferon-$\gamma$ On A Variety Of Normal And Transformed Human And Mouse Cell Lines", *Eur. J. Cancer Clin. Oncol.*, 22, pp. 419–26 (1986); B. D. Williamson et al., "Human Tumor Necrosis Factor Produced By Human B-Cell Lines: Synergistic Cytotoxic Interaction With Human Interferon", *Proc. Natl. Acad. Sci. USA*, 80, pp. 5397–401 (1983); see also European patent application 131,789]. Although TNF has shown promise as a potent cytotoxic agent, its usefulness as a therapeutic for treating malignant and non-malignant diseases has been restricted by dose-limiting toxic side effects.

TNF has been suggested as one of the mediators in the pathogenesis of endotoxic shock [B. Beutler et al., "Passive Immunization Against Cachectin/Tumor Necrosis Factor Protects Mice From Lethal Effect Of Endotoxin", *Science*, 229, pp. 869–71 (1985); B. Beutler and A. C. Cerami, "Cachectin And Tumor Necrosis Factor As Two Sides Of The Same Biological Coin", *Nature*, 320, pp. 584–88 (1986)]. In addition to its contribution to such systemic effects, TNF can play a role in local inflammation as in osteoarthritis [J. M. Dayer et al., "Cachectin/ Tumor Necrosis Factor Stimulates Collagenase And Prostaglandin $E_2$ Production By Human Synovial Cells And Dermal Fibroblasts", *J. Exp. Med.*, 162, pp. 2163-68 (1985)].

The role of TNF in such pathogeneses may be attributable to its stimulation of prostaglandin or thromboxane production. Although there is no clear explanation of the pathogenic mechanisms in toxic shock, substantial increases in circulating prostaglandins have also been reported in a variety of experimental models for hemorrhagic and endotoxic shock and the thromboxane $PGI_2$, as well as the prostaglandin $PGE_2$, have been proposed as important mediators in the development of irreversible shock [J. R. Fletcher, in *Biological Protection With Prostaglandins*, I, pp. 65-72 (1985); R. R. Butler et al., "Elevated Plasma Levels Of Thromboxane (Tx) and Prostacyclin ($PGI_2$) In Septic Shock", *Circ. Shock*, 8, pp. 213-14 (1981); R. H. Demling et al., *Am. J. Physiol.*, 240, pp. H348-53 (1981); W. C. Wise et al., "Implications For Thromboxane $A_2$ In The Pathogenesis Of Endotoxic Shock", *Adv. Shock Res.*, 6, p. 83 (1981); H. Bult et al., "Blood Levels Of 6-Keto-$PGF_{1\alpha}$, The Stable Metabolite Of Prostacyclin During Endotoxin-Induced Hypotension", *Arch. Int. Pharmacodyn*, 236, pp. 285-86 (1978); J. A. Cook et al., "Elevated Thromboxane Levels In The Rat During Endotoxic Shock", *J. Clin. Invest.*, 65, pp. 227-30 (1980)]. Although it has been reported that non-steroidal anti-inflammatory drugs appear to protect against certain lethal effects of endotoxin in experimental animals, such agents have not been used clinically to treat human patients in endotoxic and hemorrhagic shock [B. L. Short et al., "Indomethacin Improves Survival In Gram-Negative Sepsis", *Adv. Shock Res.*, 6, pp. 27-36 (1981); P. M. Almqvist et al., "Treatment Of Experimental Canine Endotoxin Shock With Ibuprofen, A Cyclooxygenase Inhibitor", *Circ. Shock*, 131, pp. 227-32 (1984); E. R. Jacobs, *J. Clin. Invest.*, 70, pp. 536-41 (1982) P. V. Halushka et al., "Protective Effects Of Aspirin In Endotoxic Shock," *J. Pharmacol. Exp. Therm.*, 218, pp. 464-69 (1981)].

To date, therefore, conventional methods and therapeutic agents have not proved to be effective in the treatment of many malignant and non-malignant diseases. Accordingly, the need exists for therapeutic agents and methods which avoid the disadvantages of these conventional agents and methods while providing effective treatment for these diseases.

DISCLOSURE OF THE INVENTION

The present invention solves the problems referred to above by providing effective combinations and methods for the treatment of malignant and non-malignant diseases. According to this invention, natural or recombinant tumor necrosis factors ("TNFs") are used in combination with non-steroidal anti-inflammatory agents for treating malignant and non-malignant neoplastic diseases. Advantageously, the combinations and methods of this invention prevent or reduce the potential side effects of treatments with high dosages of TNF alone, while not interfering with the cytotoxic activity of TNF against undesirable malignant or non-malignant cell proliferations.

BEST MODE OF CARRYING OUT THE INVENTION

Figure 1A:
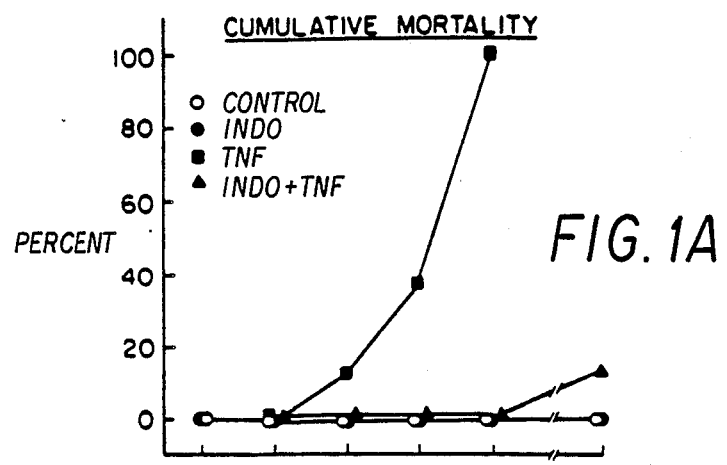
FIG. 1 is a graphical representation of the effect of treatment with TNF alone, indomethacin alone, or a combination of TNF and indomemethacin, on the mortality (FIG. 1A) and body temperature (FIG. 1B) of CD strain male rats.

In order that the invention herein described may be more fully understood, the following detailed description is set forth.

In the description, the following terms are employed:

TNF (or tumor necrosis factor)—TNF is a growth inhibitory or cytotoxic monokine. Natural TNF is a protein with a subunit molecular weight of over 17,000. TNF has been produced in small quantities in vivo. For example, endotoxin may be used to trigger the release of TNF by activated macrophages. TNF can also be induced in established cell lines, i.e., U937 [D. J. Camerson, *Reticuloenthel. Soc.*, 34, pp. 45-52 (1983)]. TNF has been cloned and expressed in various host-vector systems [A. L. Marmenout et al., "Molecular Cloning And Expression Of Human Tumor Necrosis Factor And Comparison With Mouse Tumor Necrosis Factor", *Eur. J. Biochem.*, 152, pp. 515-22 (1985); L. Fransen et al., "Molecular Cloning Of Mouse Tumor Necrosis Factor cDNA And Its Eukaryotic Expression", *Nucl. Acids Res.*, 13, pp. 4417 et seq. (1985); see also D. Pennica et al., "Human Tumour Necrosis Factor: Precursor Structure, Expression, And Homology To Lymphotoxin", *Nature*, 312, pp. 724-29 (1984); T. Shirai, "Cloning And Expression In *Escherichia Coli* Of The Gene For Human Tumour Necrosis Factor", *Nature*, 313, pp. 803-06 (1985); A. M. Wang et al., "Molecular Cloning Of The Complementary DNA For Human Tumor Necrosis Factor", *Science*, 228, pp. 149-54 (1985)].

The nucleotide sequence of cloned TNF indicates that it is composed of approximately 157 amino acids. As used in this application, "TNF" includes all proteins, polypeptides, and peptides which are natural or recombinant TNFs, or derivatives thereof, and which are characterized by the tumoricidal or cytotoxic activity of these TNFs. They include TNF-like compounds from a variety of sources, such as natural TNFs, recombinant TNFs, and synthetic or semi-synthetic TNFs.

As used in this application, "TNF" also includes the closely-related polypeptide lymphotoxin, also known as TNF-$\beta$. [D. Pennica et al., *supra*, *Nature*, 312, pp. 724-29; P. W. Gray et al., "Cloning And Expression Of cDNA For Human Lymphotoxin, A Lymphokine With Tumour Necrosis Activity", *Nature*, 312, pp. 721-24 (1984); B. Y. Rubin et al., "Purification And Characterization Of A Human Tumor Necrosis Factor From The LukII Cell Line," *Proc. Natl. Acad. Sci. USA*, 82, pp. 6637-41 (1985).]

Malignant Disease—Any disease characterized by tumorigenic or neoplastic cell growth, including malignant hematological systemic diseases, carcinomas, sarcomas, myelomas, melanomas, leukemias, lymphomas and papillomas.

Non-Malignant Neoplastic Disease—Any disease characterized by an undesirable proliferation of cells which is localized to the site of origin, such as benign growths.

This invention relates to combinations and methods for treating malignant and non-malignant neoplastic diseases. More particularly, this invention relates to combinations of pharmaceutically effective amounts of TNF and pharmaceutically effective amounts of non-steroidal anti-inflammatory agents that block the side effects of high dosages of TNF. Such side effects include hypothermia, metabolic acidosis, hypoglycemia, peripheral cyanosis, diarrhea and other effects similar to those seen in endotoxic shock. According to one embodiment, the method of this invention comprises the step of treating a mammal in a pharmaceutically acceptable manner with a pharmaceutically effective amount of TNF and a pharmaceutically effective amount of a compound selected from the group consisting of non-steroidal anti-inflammatory agents for a period of time sufficient to exert cytotoxic or cytostatic effects against the tumor or other neoplastic cell population.

Among the TNFs useful in the combinations and methods of this invention are the TNFs produced in vitro by a variety of cells in response to various inducers. For example, these TNFs include compounds displaying TNF activity obtained from sera of mice and rabbits which have been infected with Bacillus-Calmette-Guerin (BCG) or *Corynebacterium* and treated with lipopolysaccharide (LPS) of *Escherichia coli* [E. A. Carswell et al., "An Endotoxin-Induced Serum Factor That Causes Necrosis Of Tumors", *Proc. Natl. Acad. Sci. USA*, 72, pp. 3666–70 (1975)]. Also useful are the TNFs derived from the incubation media of macrophage-enriched peritoneal exudate cells of mice infected with BCG, as well as from macrophage-like tumor cells (PU5-1.8) and peritoneal macrophages of pretreated mice, which have been propagated in vitro with macrophage growth factor and stimulated with LPS [B. B. Aggarwal et al., *J. Biol. Chem.*, 260, pp. 2345–54 (1985); D. Mannel et al., "Macrophages As A Source Of Tumoricidal Activity (Tumor Necrotizing Factor)", *Infect. Immunol.*, 30, pp. 523–30 (1980)].

Furthermore, human monocytes isolated from the blood of healthy human donors, and stimulated with lymphokines or LPS, produce chemical agents having cytotoxic or cytostatic effects on mouse target cells and human transformed cells which are useful in the compositions of this invention [N. Matthews, "Production Of An Anti-tumor Cytotoxin By Human Monocytes: Comparison Of Endotoxin, Interferons And Other Agents As Inducers", *Br. J. Cancer*, 45, pp. 615–17 (1982); J. Hammerstrøm, "Soluble Cytostatic Factor(s) Released From Human Monocytes: I. Production And Effect On Normal And Transformed Human Target Cells", *Scand. J. Immunol.*, 15, pp. 311–18 (1982)]. Also useful is a fraction of the $\alpha_1$–$\alpha_2$ globulins from the serum of normal humans shown to be toxic to tumors in mice and to inhibit the growth in vitro of human colon cancer, melanoma and neuroblastoma cell lines [United States patent 4,309,418; S. Green et al., *Cancer Letters*, 6, pp. 235–40 (1979); *J. Cell. Biol.*, 79, p. 67 (1978)].

These natural animal and human TNFs have been subsequently purified to some extent and partially characterized. [See, for example, U.S. Pat. No. 4,309,418; S. Green et al., "Partial Purification Of A Serum Factor That Causes Necrosis Of Tumors", *Proc. Nat. Acad. Sci. USA*, 73, p. 381 (1976)].

TNFs useful in the combinations and methods of this invention may also be produced and purified in large amounts using recombinant DNA technology [L. Fransen et al., "Molecular Cloning Of Mouse Tumour Necrosis Factor cDNA And Its Eukaryotic Expression", *Nucl. Acids Res.*, 13, pp. 4417 et seq. (1985); A. L. Marmenout et al., "Molecular Cloning And Expression Of Human Tumor Necrosis Factor And Comparison With Mouse Tumor Necrosis Factor", *Eur. J. Biochem.*, 152, pp. 515–22 (1985); see also D. Pennica et al., *Nature*, 312, pp. 724–28 (1984); T. Shirai, *Nature*, 313, pp. 803–06 (1985); A. M. Wang . et al., *Science*, 228, pp. 149–54 (1985)].

The anti-inflammatory agents useful in the combinations and methods of this invention include non-steroidal anti-inflammatory agents that are also cyclooxygenase inhibitors, which inhibit the biosynthesis of prostaglandins, prostacyclins or thromboxanes. Such agents inhibit the arachidonic acid cyclooxygenase, which is also known as prostaglandin synthetase. These non-steroidal anti-inflammatory agents include, but are not limited to, acetyl salicylic acid (aspirin), methyl salicylate, sodium salicylate, phenylbutazone, oxyphenbutazone, apazone, indomethacin, sulindac, tolmetin, mefenamic acid, ibuprofen, naproxen, fenoprofen, flurbiprofen, ketoprofen and other compounds having a similar ability to block prostaglandin, prostacyclin or thromboxane synthesis. Other anti-inflammatory agents useful in the combinations and methods of this invention are lipocortins derived from natural sources or lipocortins and lipocortin-like polypeptides produced by recombinant techniques [see U.S. Pat. application Ser. Nos. 690,146; 712,376; 765,877 and 772,892; B. Wallner et al., "Cloning And Expression Of Human Lipocortin A Phospholipase A-2 Inhibitor With Potential Anti-Inflammatory Activity", *Nature*, 320, pp. 77–81 (1986)]and uromodulin [A. V. Muchmore and Jean M. Decker, "Uromodulin: A Unique 85-Kilodalton Immunosuppressive Glycoprotein Isolated From Urine Of Pregnant Women", *Science*, 229, pp. 479–81 (1985)].

The combinations and methods of the present invention allow the administration of TNF in higher doses than those tolerated in conventional treatment regimens based upon TNF alone. Accordingly, the combinations and methods of this invention advantageously reduce or eliminate the toxic effects of high dose treatments with TNF alone. Without being bound by theory, we believe that the effectiveness of our combinations and methods over those using TNF alone is due to the action of the anti-inflammatory agents in blocking the production of one or more of the prostaglandins, prostacyclins or thromboxanes in the body resulting from high dosages of TNF, thereby reducing the toxicity of TNF. This allows the administration of TNF in high doses formerly typically accompanied by toxic effects. Thus, the use of TNF in combination with a non-steroidal anti-inflammatory agent may reduce the duration and level of treatment which would be required by therapies based upon conventionally tolerated lower dosages of TNF alone.

The combinations and methods of this invention are useful in treating any mammal, including humans. TNFs derived from the target patient species are preferably used. However, TNFs derived from other species may be used in the combinations and methods of this invention if they are active in the target cells. For example, mouse TNF has been shown to be active in human cell lines in vitro [L. Fransen et al., "Recombinant Tumor Necrosis Factor: Species Specificity For A Variety Of Human And Murine Transformed Cell Lines", *Cell. Immunol.*, 100, pp. 260-67 (1986)].

According to this invention, mammals are treated with pharmaceutically effective amounts of the two active components—TNF and a non-steroidal anti-inflammatory agent—of the combinations of this invention for a period of time sufficient to inhibit malignant or undesirable non-malignant cell proliferation, e.g., suppress tumor or neoplastic cell growth, and preferably to kill tumor or neoplastic cells.

In accordance with this invention, pharmaceutically effective amounts of a non-steroidal anti-inflammatory agent and the TNF are administered sequentially or concurrently to the patient. However, the particular sequence of treatment does not appear to be important. The most effective mode of administration and dosage regimen of TNF and anti-inflammatory agent will depend upon the type of disease to be treated, the severity and course of that disease, previous therapy, the patient's health status and response to TNF and the judgment of the treating physician. TNF may be administered to the patient at one time or over a series of treatments.

Preferably, the non-steroidal anti-inflammatory agent and the TNF are administered sequentially to the patient, with the non-steroidal anti-inflammatory agent being administered before, after, or both before and after treatment with TNF. Sequential administration involves treatment with the non-steroidal anti-inflammatory agent at least on the same day (within 24 hours) of treatment with TNF and may involve continued treatment with the anti-inflammatory agent on days that the TNF is not administered. Conventional modes of administration and standard dosage regimens of anti-inflammatory agents may be used. [See A. G. Gilman et al. (Eds.), *The Pharmacological Basis Of Therapeutics*, pp. 697-713, 1482, 1489-91 (1980); *Physicians Desk Reference*, (1986 Edition).] For example, indomethacin may be administered orally at a dosage of about 25-50 mg, three times a day. Higher doses may also be used. Alternatively, aspirin (about 1500-2000 mg/day), ibuprofen (about 1200-3200 mg/day), or conventional therapeutic doses of other non-steroidal anti-inflammatory agents may be used. Dosages of non-steroidal anti-inflammatory agents may be titrated to the individual patient.

According to one embodiment of this invention, the patient may receive concurrent treatments with the non-steroidal anti-inflammatory agent and TNF. Local, intralesional or intravenous injection of TNF is preferred. [See A. G. Gilman et al., supra at pp. 1290-91.] The non-steroidal anti-inflammatory agent should preferably be administered by subcutaneous injection or orally.

Alternatively, the patient may receive a composition comprising a combination of TNF and a non-steroidal anti-inflammatory agent according to conventional modes of administration of agents which exhibit anti-cancer, antitumor or anti-inflammatory activity. These include, for example, parenteral, subcutaneous, intravenous or intralesional routes of administration.

The compositions used in these therapies may also be in a variety of forms. These include, for example, solid, semi-solid and liquid dosage forms, such as tablets, pills, powders, liquid solutions or suspensions, liposomes, suppositories, injectable and infusable solutions. The preferred form depends on the intended mode of administration and therapeutic application. The compositions also preferably include conventional pharmaceutically acceptable carriers and adjuvants which are known to those of skill in the art. Preferably, the compositions of the invention are in the form of a unit dose and will usually be administered to the patient one or more times a day.

TNF may be administered to the patient in any pharmaceutically acceptable dosage form including intravenous, intramuscular, intralesional or subcutaneous injection. An effective dose may be in the range of from about 0.01 to about 1.0 mg/kg body weight, it being recognized that lower and higher doses may also be useful. More particularly, doses of TNF higher than those typically tolerated in patients treated with TNF alone may advantageously be used in the methods and compositions of this invention.

It should, of course, be understood that the compositions and methods of this invention may be used in combination with other cancer or tumor therapies, e.g., interferons (e.g., IFN-$\alpha$, IFN-$\beta$ and IFN-$\gamma$) or chemotherapy, for the treatment of malignant and non-malignant diseases in mammals.

Once improvement of the patient's condition has occurred, a maintenance dose is administered if necessary. Subsequently, the dosage or the frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

In order that the invention described herein may be more fully understood, the following examples are set forth. It should be understood that these examples are for illustrative purposes only, and are not to be construed as limiting this invention in any manner.

EXAMPLE 1

This example represents the in vivo action of non-steroidal anti-inflammatory agents in blocking the toxic side effects of treatment with high doses of TNF. In this example, we administered TNF at a dosage which was lethal when given by an intravenous route, due to life-threatening side effects such as hypothermia, metabolic acidosis, hypoglycemia and peripheral cyanosis. This dose would have been well tolerated if given subcutaneously, because blood levels of TNF attained via that route are never as high as those resulting from intravenous administration.

The data set forth below show that much higher blood levels of TNF are tolerated, without side effects, when TNF is administered in combination with a non-steroidal anti-inflammatory agent rather than alone. Accordingly, this example demonstrates that treatment with a non-steroidal anti-inflammatory agent concurrently with the administration of TNF blocks any adverse physiological responses induced by high blood levels of TNF. The methods and compositions of this invention, therefore, advantageously enhance the usefulness of TNF, particularly at high doses formerly typically associated with undesirable side effects, as a therapeutic agent for treating malignant and non-malignant neoplastic diseases.

In this example, male rats (CD strain, Charles River Breeding Laboratories, Wilmington, Mass.) weighing 50–60 grams each, were divided into six treatment groups. All the rats were maintained on a standard diet of Purina Rat Chow and water for 3 days prior to treatment. We treated each of Groups 1–5 with either TNF alone, an anti-inflammatory agent alone, or TNF in combination with an anti-inflammatory agent, as indicated below. Group 6 served as a vehicle control group.

Group 1: 4 µg/g body weight human recombinant TNF intravenously.

Group 2: 3 mg/kg body weight indomethacin intraperitoneally; followed by 4 µg/g body weight human recombinant TNF intravenously 2 hours later.

Group 3: 3 mg/kg body weight indomethacin intraperitoneally; phosphate buffered saline intravenously 2 hours later.

Group 4: 20 mg/kg body weight ibuprofen intraperitoneally; followed by 4 µg/g body weight human recombinant TNF intravenously 2 hours later.

Group 5: 20 mg/kg body weight ibuprofen intraperitoneally; phosphate buffered saline intravenously 2 hours later.

Group 6: vehicle control (-) phosphate buffered saline intraperitoneally and intravenously.

The TNF used in this example was recombinant human TNF, supplied by Biogent (Ghent, Belgium) and Biogen Inc. (Cambridge, Mass.). The preparation was more than 99% pure, contained less than 20 ng/mg endotoxin and had a specific activity in the range of about $9.6 \times 10^6$ units/mg to $2.5 \times 10^7$ units/mg. The indomethacin and ibuprofen were supplied by Sigma Co. and Upjohn Co., respectively.

TNF was administered by intravenous injection into the jugular vein performed under ether anesthesia. We collected blood samples by puncture of the jugular vein before and at hourly intervals after TNF or phosphate buffered saline injection. We then centrifuged the collected blood in heparinized tubes and stored the plasma at $-20°$ C. We measured plasma glucose levels using a Beckman Glucose Analyzer (Beckman Instruments Co.). Prostaglandin metabolite levels were measured by radioimmunoassay as described in L. Levine, *Biochem. of Arach. Acid Metab.*, pp. 405–16 (1985). Rectal temperatures were measured using an electronic thermometer (Model 49TA, Yellow Springs Instrument Co., Inc.). All results are expressed as Means ±SEM and the statistical significance of changes seen were evaluated with the Unpaired Student's t test.

Effect Of TNF Treatment Alone

As demonstrated in FIG. 1A, among the Group 1 rats, no deaths occurred during the first hour post-TNF injection. After that time, however, a progressive loss in viability was observed, with death of all the animals typically resulting within a period of 2 to 4 hours. For example, by 2 hours post-injection, about 25% of the animals had died and by 4 hours post-injection, all of the Group 1 rats were dead. In total, 35 animals were treated in this fashion, and 30 died this rapidly.

The rapid decrease in viability of the Group 1 rats was accompanied by a spectrum of physiological changes resembling those observed in studies of experimentally-induced endotoxic shock [J. P. Filkins, *Am. J. Emerg. Med.*, 2, pp. 70–73 (1984) J. P. Filkins, *Fed. Proc.*, pp. 300–04 (1985)]. These physiological changes included hypothermia, peripheral cyanosis, metabolic acidosis, diarrhea, initial hyperglycemia followed by severe hypoglycemia, and increased prostaglandin synthesis.

Figure 1B:
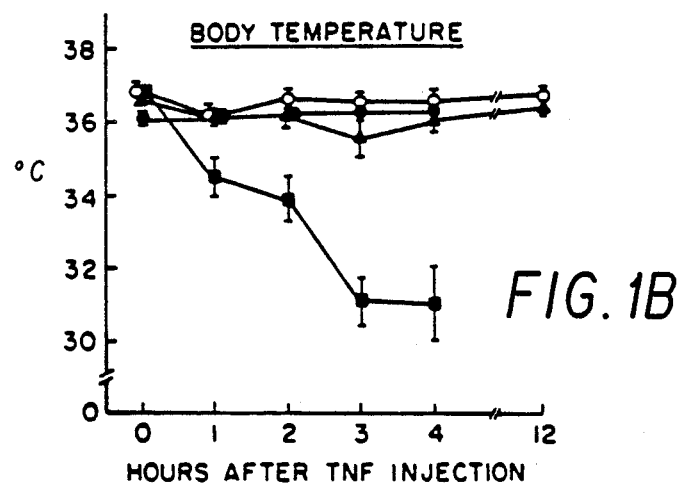

As demonstrated in FIG. 1B, TNF induced a sharp decrease in body temperature within 1 hour post-injection, with the mean rectal temperature of the treated animals falling from $36.8°$ C. to $34.3°$ C. This decrease in temperature clearly preceded other symptoms and, therefore, appeared to be a specific physiological effect of TNF, rather than a consequence of the loss of viability. Between 3 and 4 hours post-injection, body temperatures continued to decrease to between $29.5°$ C. and $32°$ C. This hypothermic effect is surprising, since lower intravenous doses of TNF, or the equivalent amount of TNF injected subcutaneously, induced a fever which was blocked with cyclooxygenase inhibitors.

Other physiological changes accompanied the hypothermia. For example, in the final hour before death, the animals appeared very lethargic and showed cyanosis in their extremities. In addition, at about 1 hour post-injection, the animals had diarrhea. Upon postmortem examination, the intestines of the TNF-treated rats appeared empty, even though the animals had free access to food prior to treatment. In contrast, the intestines of the control rats or of control rats deprived of food for 4 hours were full of solid material.

Another result of the TNF treatment was initial hyperglycemia, followed by severe hypoglycemia. As demonstrated in FIG. 2, large biphasic changes in blood glucose resulted after the TNF injections. Initially, the rats developed hyperglycemia which, within one hour, was followed by a sharp decrease in plasma glucose levels to about 30 mg/ 100 ml (1.6mM). Four hours after the TNF injection, when most of the animals were near death, their blood glucose levels had fallen further to about 20 mg/ 100 ml. Such levels, if maintained, are not generally sufficient for survival.

The TNF-treated rats also exhibited increased prostaglandin levels in their blood serum. By determining the blood content of the stable metabolite of $PGE_2$, 13,14-dihydro-115-keto-PGE2 ("DHK-PG"), we measured body prostaglandin production after TNF treatment. Within 1 hour post-injection, TNF induced a substantial increase in $PGE_2$ production. As shown in Table 1, plasma levels of DHK-PG increased ten-fold, from $0.40 \pm 0.05$ ng/ml to $4.26 \pm 0.48$ ng/ml. The high levels of this metabolite of $PGE_2$ were maintained for several hours, and at 3 hours post-injection, reached $5.77 \pm 0.51$ ng/ml. These increases were unexpected since prostaglandins and, in particular, $PGE_2$, have been associated with the induction of fever rather than hypothermia [H. A. Bernheim et al., *J. Physiol.*, 301, pp. 69–78 (1980)].

In treatments similar to those described above for Groups 1–3 and 6, we observed that TNF treatment also resulted in severe metabolic acidosis.

As shown in Table 2, we measured blood pH, $pCO_2$ (mm Hg) and $HCO_3$ (µmol/1) in four separate groups of rats treated as follows:

Group A (4 rats): vehicle control-phosphate buffered saline intravenously.

Group B (8 rats): 4 µg/g body weight human recombinant TNF intravenously.

Group C (7 rats): 3 mg/kg body weight indomethacin intraperitoneally; followed by 4 µg/g body weight human recombinant TNF intravenously 2 hours later.

Group D (5 rats): 3 mg/kg body weight indomethacin intraperitoneally; followed by phosphate buffered saline intravenously 2 hours later.

We collected arterial blood from the abdominal aorta under ether anesthesia in heparinized syringes 3 hours after TNF or saline injection. We measured blood pH and pCO$_2$ (mm Hg) in a Blood Gas Analyzer. HCO$_3$ (μmol/l) was measured using the Henderson-Hasselbach Equation. As shown in Table 2, the arterial pH of rats treated with TNF alone fell significantly, their pCO$_2$ decreased by about 30%, and their arterial bicarbonate (HCO$_3$) concentration was about half that in the controls.

The physiological effects resulting from the TNF treatment are typical of those observed in animals with endotoxic shock. Accordingly, although activated monocytes produce many potent polypeptides, overproduction of TNF may by itself account for most of the life-threatening symptoms of irreversible shock.

In order to verify that the various physiological effects observed were not due to endotoxin contamination of the TNF solutions themselves, we heated the TNF at 70° C. for 15 minutes to destroy TNF activity but not to affect any endotoxins [E. A. Carswell et al., supra, p. 1]. Administration of the thus-treated TNF to rats did not cause the death of any animal. In addition, none of the treated rats exhibited changes in body temperature or developed diarrhea.

Effect Of Combination Non-Steroidal Anti-Inflammatory/TNF Treatments

The Group 2 and Group 4 rats treated with a single intraperitoneal injection of a non-steroidal anti-inflammatory/prostaglandin synthetase inhibitor before receiving TNF treatment, did not exhibit the symptoms seen in the Group 1 rats. Thus, indomethacin (Group 2) and ibuprofen (Group 4) were found to prevent the toxic effects of high dosage levels of TNF administration.

As demonstrated in FIG. 1A, a single injection of indomethacin before TNF treatment provided a high degree of protection against the lethal effects of TNF. All of the Group 2 rats were alive 4 hours after receiving the TNF injection. For example, among eight Group 2 rats, one rat died 12 hours after that injection and two more rats died 21 hours after that injection. The other five rats in Group 2 remained alive and appeared normal subsequently.

In treatments similar to those described above for Group 1 and Group 2 rats, we again observed that a single injection of indomethacin provided protection against TNF-induced mortality. More specifically, while each of a group of 16 rats injected with TNF alone died within 4 hours of treatment, each of the group of 20 rats treated with indomethacin prior to TNF treatment were alive 4 hours after receiving the TNF injection. Four of the indomethacin-treated rats died within the period of 4-6 hours after the TNF injection and three more rats died within 6-24 hours after that injection. No further deaths occurred within the period of 24-56 hours post-TNF injection, at which time 65% of the rats were viable and appeared healthy.

Similarly, we observed that rats who received a single injection of indomethacin after TNF treatment were protected against the lethal effects of TNF. While animals receiving only TNF all died within 4 hours of treatment, rats who were treated with indomethacin one hour after TNF administration were alive 6 hours after the TNF injection.

Figure 3A:
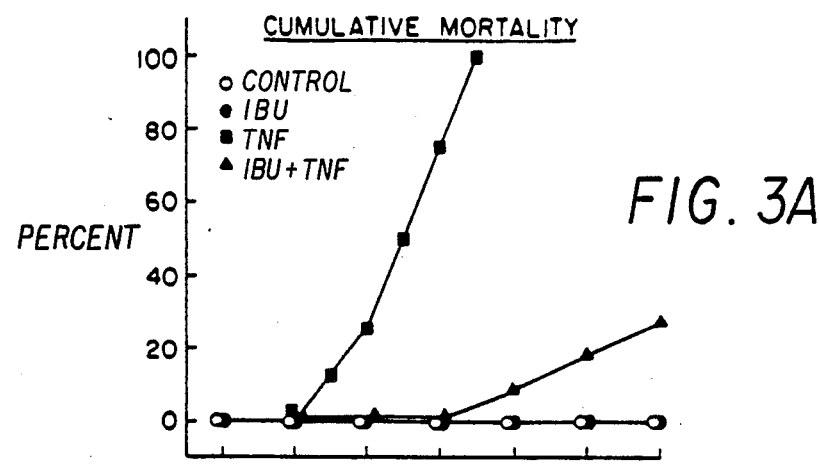
FIG. 3 is a graphical representation of the effect of treatment with TNF alone, ibuprofen alone, or a combination of TNF and ibuprofen, on the mortality (FIG. 3A) and body temperature (FIG. 3B) of CD strain male rats.

The Group 4 rats, who received a single injection of ibuprofen before TNF treatment were also protected against the lethal effects of TNF. As demonstrated in FIG. 3A, 75% of the ibuprofen-treated rats were still alive 6 hours after the TNF injection. By 24 hours after TNF treatment, 55% of the rats were viable and appeared healthy.

We believe that repeated administration of indomethacin or ibuprofen in the treatments described above would have further reduced any TNF induced mortality.

Figure 3B:
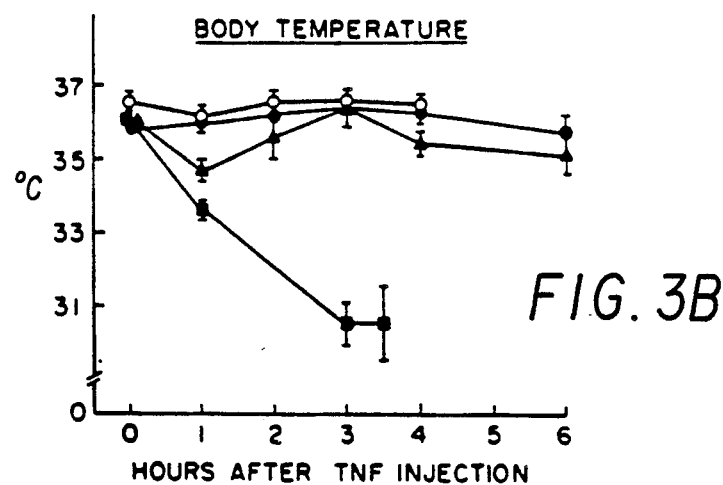

Both indomethacin and ibuprofen prevented the rapid decrease in body temperature and the subsequent progressive hypothermia seen in animals treated with TNF alone. As demonstrated in FIGS. 1B and 3B, several of the rats treated with indomethacin or ibuprofen before TNF treatment showed only a slight decrease in body temperature—1° or 2° C.—which quickly returned to normal levels. Furthermore, when indomethacin was administered to five rats 1 hour after TNF treatment, when hypothermia was already evident, their temperatures rose and returned to normal.

The Group 2 (indomethacin-treated) and Group 4 (ibuprofen-treated) rats exhibited neither peripheral cyanosis nor diarrhea.

In addition, administration of indomethacin or ibuprofen before TNF treatment completely blocked the large rise in prostaglandin production, as reflected in the serum levels of the DHK-PG metabolite of PGE$_2$, which was seen in those rats treated with TNF alone. As demonstrated in Table 1, levels of this metabolite were extremely low in the indomethacin and ibuprofen-treated rats. By 3 hours after injection of the cyclooxygenase inhibitor, although DHK-PG levels were again detectable and approached normal values, they were still much lower than DHK-PG levels in the rats treated only with TNF.

Figure 2:
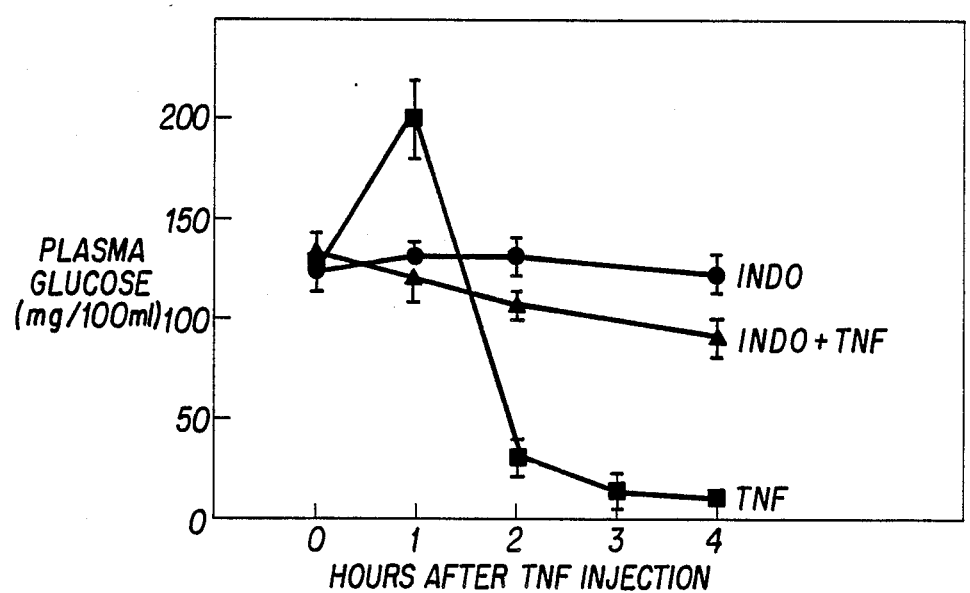
FIG. 2 is a graphical representation of the effect of treatment with TNF alone, indomethacin alone, or a combination of TNF and indomethacin, on plasma glucose levels of CD strain male rats.

The biphasic changes in plasma glucose levels seen in the TNF-treated rats of Group 1 were not seen in the rats receiving either an indomethacin or an ibuprofen injection prior to TNF treatment. As shown in FIG. 2, the Group 2 rats who received indomethacin did not show any significant changes in plasma glucose levels. Ibuprofen injection before TNF treatment also decreased the changes in blood glucose. Four hours after the TNF treatment, those rats who had received ibuprofen had glucose levels which were about 40% lower than the untreated control rats. This decrease in blood glucose was much smaller than that seen in the Group 1 rats who were treated with TNF alone.

The significant change in blood pH, pCO$_2$ and HCO$_3$ levels which accompanied TNF treatment alone was not seen in rats treated with indomethacin prior to injection with TNF. As shown in Table 2, the bicarbonate (HCO$_3$) levels of rats that received indomethacin prior to injection with TNF were 50% higher than animals that received only TNF. Three hours after TNF injection, the arterial pCO$_2$ and pH of the indomethacin-treated rats were indistinguishable from those of the control rats.

While the reduction in TNF side effects demonstrated above resulted from a single administration of a non-steroidal anti-inflammatory agent, we believe that remaining side effects would be further reduced or eliminated by repeated administration of that agent over the course of TNF therapy.

EXAMPLE 2

Figure 4:
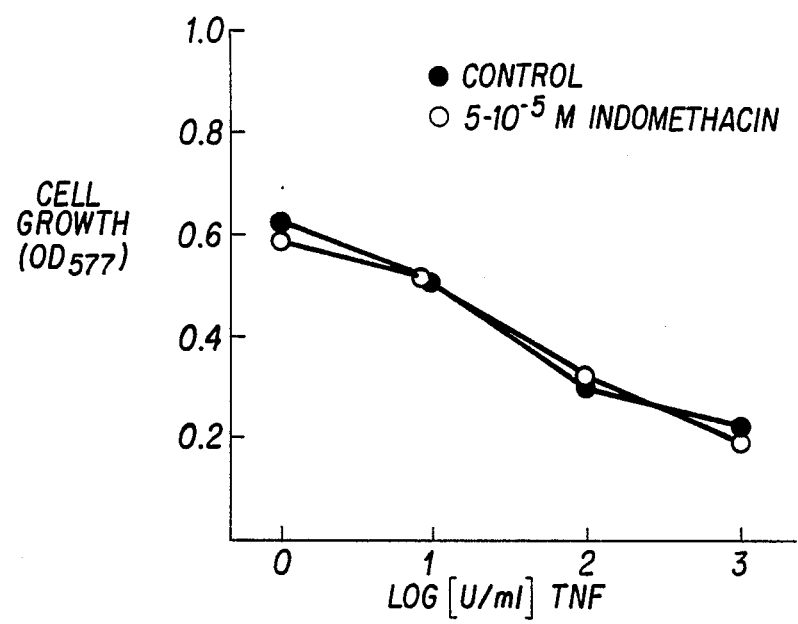
FIG. 4 is a graphical representation of the effect of treatment with TNF alone, or in combination with indomethacin, on cell growth of cultured Hela cells.

In this example, we examined the effect of non-steroidal anti-inflammatory agents on the cytotoxic and cytostatic actions of TNF on various transformed cell lines. As shown in FIG. 4, the cytostatic action of TNF on cultured tumor cells (Hela cells) was not affected by the presence of indomethacin at concentrations that should prevent all prostaglandin synthesis.

Hela D98/AH2 cells (a cell line originally obtained from Dr. E. Stanbridge, University of California at Irvine) were cultured in Dulbecco's modified Eagle's medium (DMEM) containing 10% fetal calf serum and 25 μg/ml gentamycin at 37° C. under 5% $CO_2$, as described in L. Fransen et al., *Europ. J. Cancer Clin. Oncol.*, 22, 419–26 (1986). We plated $10^4$ cells/0.2ml/well in standard microtiter plates containing various concentrations of TNF or TNF and indomethacin. TNF was tested at concentrations of 3000 units/ml and ⅓ dilutions down to 1 unit/ml. At each TNF concentration, indomethacin was tested at concentrations of $5 \times 10^{-5}$M (a concentration which completely blocks prostaglandin synthesis) and ⅓ dilutions down to $5 \times 10^{-7}$M. After 3 days, we removed the cell supernatant and quantitated the remaining cells by staining them for 10 minutes with a solution of 0.5% crystal violet, 8% (V/V) formaldehyde (40%), 0.17% NaCl and 22.3% (V/V) ethanol. The wells were then thoroughly washed with tap water, and the bound dye was dissolved in 33% acetic acid (0.1 ml/well). The released dye was measured spectrophotometrically at 577 nm (Kontron spectrophotometer SLT 210). The results are shown in FIG. 4, in which increasing cytotoxicity corresponds to decreasing OD-577 values.

Similar results were observed on the mouse fibroblast cell line L929 and with the human cervix carcinoma cell line ME-180.

As demonstrated in this example, cyclooxygenase inhibitors, such as indomethacin, reduce the toxic effects of high doses of TNF without preventing its antineoplastic activity.

While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

The following Table 1 shows the effect of treatment with TNF alone, indomethacin alone, ibuprofen alone, or a combination of TNF and either indomethacin or ibuprofen, on plasma 13,14-dihydro-15-keto-PGE$_2$ ("DHK-PG") levels of CD strain male rats.

TABLE 1

PLASA DHK-PG (13,14-DIHYDRO-15-KETO-PGE$_2$) BEFORE AND AFTER TNF OR SALINE INTRAVENOUS ADMINISTRATION

| Rate Injected With | Time After TNF or Saline | | |
|---|---|---|---|
| | 0 Time[1] | 1 hr | 3 hr |
| | [DHK-PG (ng/ml)] | | |
| TNF (Group 1) | 0.40 ± 0.05 | 4.26 ± 0.48 | 5.77 ± 0.51 |
| Indomethacin and TNF 2 hrs later (Group 2) | 0.42 ± 0.07 | 0.08 ± 0.01 | 0.12 ± 0.02 |
| Indomethacin and Saline 2 hrs later (Group 3) | 0.35 ± 0.10 | 0.06 ± 0.01 | 0.12 ± 0.03 |
| Ibuprofen and TNF 2 hrs later (Group 4) | 0.17 ± 0.02 | a[2] | 0.69 ± 0.10 |
| Ibuprofen and Saline 2 hrs later (Group 5) | 0.17 ± 0.02 | a[2] | 0.64 ± 0.10 |

[1] 0 Time measurements were made immediately before administration of the TNF or saline.
[2] a = not determined.

The following Table 2 shows the effect of treatment with TNF alone, or in combination with indomethacin, on the blood pH, $pCO_2$ and $HCO_3$ levels of CD strain male rats.

TABLE 2

EFFECTS OF TNF AND INDOMETHACIN ON PLASMA pH, $pCO_2$ AND BICARBONATE CONCENTRATION

| | pH | $pCO_2$(mm Hg) | $HCO_3$(μmol/l) |
|---|---|---|---|
| Saline (Group A) | 7.48 ± 0.02 | 29.9 ± 0.3 | 21.4 ± 1.1 |
| TNF (Group B) | 7.33 ± 0.02[1] | 22.2 ± 2.1[1] | 11.1 ± 0.9[2] |
| Indomethacin and TNF 2 hrs. later (Group C) | 7.43 ± 0.02 | 26.0 ± 1.6 | 16.7 ± 1.0[3] |
| Indomethacin and saline 2 hrs. later (Group D) | 7.35 ± 0.06 | 39.3 ± 5.0 | 20.7 ± 0.5 |

[1] $p < 0.05$ (compared to Group A).
[2] $p < 0.01$ (compared to Group A).
[3] $p < 0.05$ (compared to Group B).

We claim:

1. A regimen for the treatment of malignant or non-malignant neoplastic diseases in mammals consisting essentially of a dosage of TNF effective to suppress tumor or neoplastic cell growth or to kill tumor or neoplastic cells in combination with a non-steroidal anti-inflammatory agent which inhibits prostaglandin, prostacyclin or thromboxane biosynthesis, in an amount effective to reduce or eliminate the toxic side effects on mammals of said dosage of TNF.

2. The regimen according to claim 1, wherein the non-steroidal anti-inflammatory agent is selected from the group consisting of acetyl salicylic acid, methyl salicylate, sodium salicylate, phenylbutazone, oxyphenbutazone, apazone, indomethacin, sulindac, tolmetin, mefenamic acid, ibuprofen, naproxen, fenoprofen, flurbiprofen, ketoprofen, lipocortin and uromodulin.

3. The regimen according to claim 1, wherein the dosage amount of TNF is between about 0.01 and 1.0 mg/kg body weight.

4. The regimen according to claim 1, wherein the TNF is selected from the group consisting of natural TNF, recombinant TNF and derivatives thereof which are characterized by the cytotoxic activity of TNF against transformed cells.

5. The regimen according to claim 4, wherein the TNF is recombinant TNF.

6. A method for reducing or eliminating the toxic side effects to mammals of TNF in a therapy comprising administering to a mammal an effective amount of TNF, said method comprising administering in conjunction with said TNF an effective amount of a non-steroidal anti-inflammatory agent which inhibits prostaglandin, prostacyclin or thromboxane biosynthesis.

7. The method according to claim 6, wherein the non-steroidal anti-inflammatory agent is selected from the group consisting of acetyl salicylic acid, methyl salicylate, sodium salicylate, phenylbutazone, oxyphenbutazone, apazone, indomethacin, sulindac, tolmetin, mefenamic acid, ibuprofen, naproxen, fenoprofen, flurbiprofen, ketoprofen, lipocortin and uromodulin.

8. The method according to claim 6, wherein the amount of TNF is between about 0.01 and 1.0 mg/kg body weight.

9. The method according to claim 6, wherein the TNF is selected from the group consisting of natural TNF, recombinant TNF and derivatives thereof which are characterized by the cytotoxic activity of TNF against transformed cells.

10. The method according to claim 9, wherein the TNF is recombinant TNF.

11. The method according to claim 6, wherein TNF and the non-steroidal anti-inflammatory agent are administered to a human.

12. The method according to claim 6, wherein TNF and the non-steroidal anti-inflammatory agent are administered to treat a malignant disease selected from the group consisting of malignant tumorigenic or neoplastic cell growth, malignant hematological systemic diseases, carcinomas, sarcomas, myelomas, melanomas, lymphomas and papillomas.

13. The method according to claim 6, wherein the effective amount of TNF is greater than the dosage generally tolerated when TNF is administered alone.

14. In a method for treating malignant and non-malignant diseases in mammals using therapeutically effective amounts of TNF to suppress tumor or neoplastic cell growth or to kill tumor or neoplastic cells, the improvement wherein a non-steroidal anti-inflammatory agent which inhibits prostaglandin, prostacyclin or thromboxane biosynthesis is administered in conjunction with the administration of said TNF in an amount effective to reduce or eliminate the toxic side effects of the TNF.

15. The improvement according to claim 14, wherein the non-steroidal anti-inflammatory agent is selected from the group consisting of acetyl salicylic acid, methyl salicylate, sodium salicylate, phenylbutazone, oxyphenbutazone, apazone, indomethacin, sulindac, tolemetin, mefenamic acid, ibuprofen, naproxen, fenoprofen, flurbiprofen, ketoprofen, lipocortin and uromodulin.

16. The improvement of claim 15, wherein the anti-inflammatory agent is co-administered with the TNF.

17. The improvement of claim 15, wherein the anti-inflammatory agent and the TNF are administered serially.

18. The improvement of claim 15, wherein the anti-inflammatory agent is indomethacin or ibuprofen.

* * * * *